United States Patent
Sablone

(10) Patent No.: US 9,714,152 B2
(45) Date of Patent: Jul. 25, 2017

(54) APPARATUS AND METHOD FOR FOLDING A WEB IN TWO

(75) Inventor: Gabriele Sablone, Montesilvano (IT)

(73) Assignee: Fameccanica.Data S.p.A., Pescara (IT)

(*) Notice: Subject to any disclaimer, the term of this patent is extended or adjusted under 35 U.S.C. 154(b) by 869 days.

(21) Appl. No.: 13/997,538

(22) PCT Filed: Nov. 10, 2011

(86) PCT No.: PCT/IB2011/055013
§ 371 (c)(1),
(2), (4) Date: Jul. 25, 2013

(87) PCT Pub. No.: WO2012/085698
PCT Pub. Date: Jun. 28, 2012

(65) Prior Publication Data
US 2013/0303354 A1   Nov. 14, 2013

(30) Foreign Application Priority Data
Dec. 23, 2010 (IT) ............... TO2010A1042

(51) Int. Cl.
*B65H 45/22* (2006.01)
*B65H 45/08* (2006.01)
*A61F 13/15* (2006.01)

(52) U.S. Cl.
CPC ....... *B65H 45/08* (2013.01); *A61F 13/15747* (2013.01); *A61F 13/15764* (2013.01); *B65H 45/22* (2013.01); *B65H 2801/57* (2013.01)

(58) Field of Classification Search
CPC ............. A61F 13/15747; B65H 45/22
(Continued)

(56) References Cited

U.S. PATENT DOCUMENTS 3,981,763 A * 9/1976 Brocklehurst .... A61F 13/15747
156/352
8,273,003 B2 * 9/2012 Umebayashi ..... A61F 13/15747
493/402
(Continued)

FOREIGN PATENT DOCUMENTS

EP          1 504 738        2/2005
JP        A-2010-227545      10/2010
(Continued)

OTHER PUBLICATIONS

Japanese Office Action issued in Japanese Patent Application No. 2013-545534.
(Continued)

*Primary Examiner* — Andrew M Tecco
*Assistant Examiner* — Chelsea Stinson
(74) *Attorney, Agent, or Firm* — Nixon & Vanderhye P.C.

(57) ABSTRACT

An apparatus for folding in two a continuous web (10) that advances in a longitudinal direction (A), comprising: a folding station (22) designed to fold said continuous web (10) along a line of longitudinal folding (B) parallel to said longitudinal direction (A); and an alignment station (24) for mutual alignment of opposite longitudinal edges (14) of said continuous web (10), wherein said alignment station (24) comprises two suction belt conveyors (42, 44) having respective branches facing one another (50, 52) designed to pick up by means of suction respective folded sections (34, 32) of said web (10), said suction belt conveyors (42, 44) being mobile in a transverse direction (D) and being associated to a control device (72) designed to move said suction belt conveyors (42, 44) by the same amount and in opposite directions in said transverse direction (D) as a function of information on the position of said longitudinal edges (14).

7 Claims, 5 Drawing Sheets

(58) Field of Classification Search
USPC .................................................... 493/9, 424
See application file for complete search history.

(56) References Cited

U.S. PATENT DOCUMENTS

| | | | | |
|---|---|---|---|---|
| 2005/0026760 A1* | 2/2005 | Yamamoto | ........ | A61F 13/15747 493/81 |
| 2005/0145150 A1* | 7/2005 | Mortell | ................. | A41B 9/001 112/475.09 |
| 2005/0181921 A1* | 8/2005 | Yamamoto | ........ | A61F 13/15747 493/81 |
| 2005/0189063 A1* | 9/2005 | Mizutani | ........... | A61F 13/15211 156/204 |
| 2008/0026925 A1* | 1/2008 | Allen | ................ | A61F 13/15682 493/423 |
| 2010/0168708 A1* | 7/2010 | Umebayashi | ..... | A61F 13/15747 604/385.03 |
| 2010/0179042 A1* | 7/2010 | Yamamoto | ........ | A61F 13/15747 493/379 |
| 2012/0207871 A1* | 8/2012 | Yamamoto | ........ | A61F 13/15747 425/335 |
| 2015/0209190 A1* | 7/2015 | Sablone | ............ | A61F 13/15723 156/227 |

FOREIGN PATENT DOCUMENTS

| | | | | |
|---|---|---|---|---|
| JP | A-2010-227546 | 10/2010 | | |
| JP | WO 2011013821 A1 * | 2/2011 | ....... | A61F 13/15747 |

OTHER PUBLICATIONS

Int'l. Search Report for PCT/IB2011/055013, mailed Feb. 29, 2012.
Written Opinion of the International Searching Authority for PCT/IB2011/055013, mailed Feb. 29, 2012.

* cited by examiner

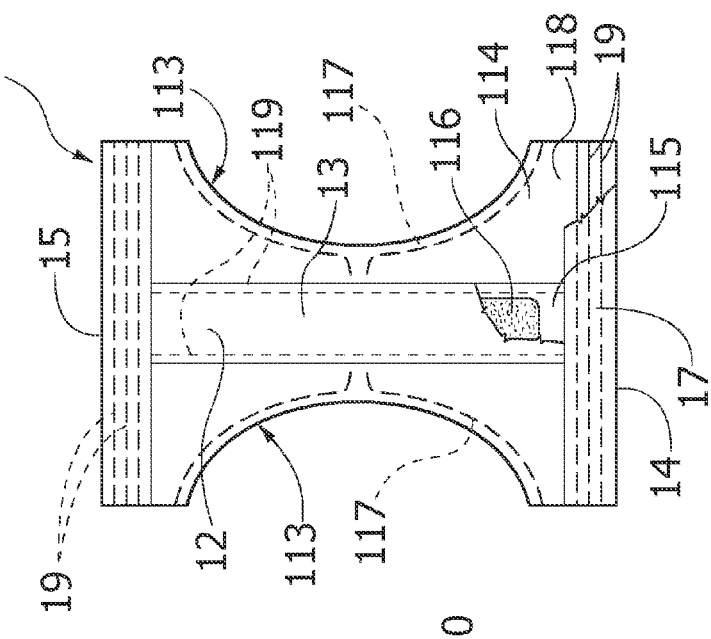
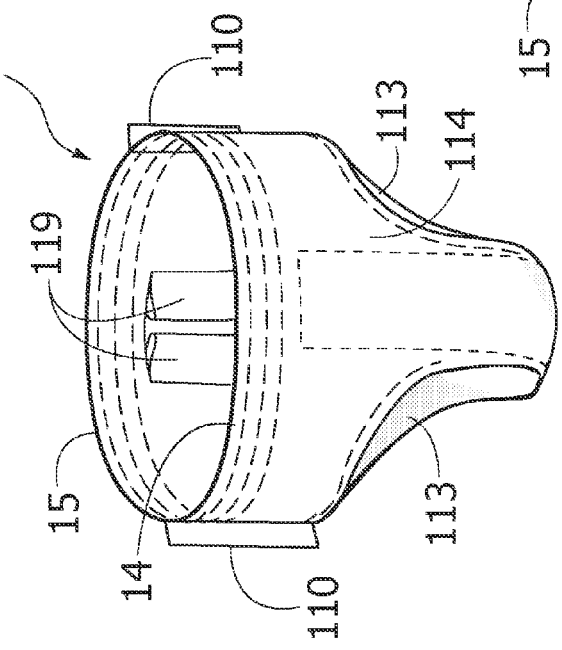
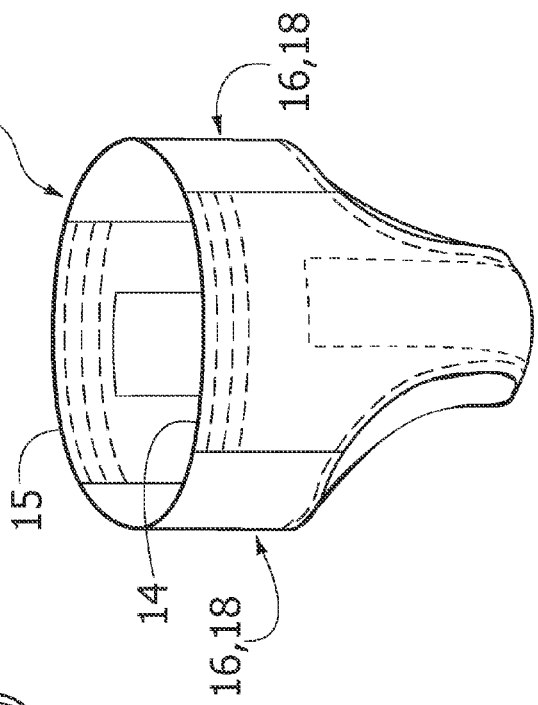

APPARATUS AND METHOD FOR FOLDING A WEB IN TWO

This application is the U.S. national phase of International Application No. PCT/IB2011/055013, filed 10 Nov. 2011, which designated the U.S. and claims priority to IT Application No. TO2010A001042, filed 23 Dec. 2010, the entire contents of each of which are hereby incorporated by reference.

FIELD OF THE INVENTION

The present invention relates to an apparatus and a method for folding in two a web that advances continuously in a longitudinal direction.

The invention has been developed in particular for the production of absorbent sanitary products that can be worn as pants. A typical example of absorbent sanitary products of this type is represented by the so-called training-pants.

DESCRIPTION OF THE PRIOR ART

A common technique for the production of sanitary products that can be worn like pants consists in providing a continuous composite web formed by a continuous chain of semifinished products set in a transverse direction with respect to the direction of movement of the web. The continuous composite web is folded in two about a longitudinal axis so as to set the opposite longitudinal edges of the web on top of one another. The opposite longitudinal edges are then connected to one another in areas of connection set apart from one another in a longitudinal direction by a pitch equal to the width of the products. The continuous chain of semifinished products is subsequently subjected to an operation of cutting in a transverse direction to form the finished product.

An example of a method of manufacture of absorbent sanitary products of this type is described in the documents Nos. EP-A-1523968 and EP-A-2025311, filed in the name of the present applicant.

In methods of this type it is necessary to ensure a mutual alignment between the opposite longitudinal edges of the continuous web during the folding step. To obtain a precise alignment of the edges it is necessary to detect the position of the longitudinal edges of the web by means of sensors and correct the relative position of the edges if the edges are not aligned to one another.

The document No. EP-A-1504738 describes a device for correcting the position of the opposite longitudinal edges of the continuous web during the folding operation. The device described in the document No. EP-A-1504738 comprises a plurality of oscillating guide rollers that are held in contact with respective lateral edge portions of the web to change the angle of the web with respect to the longitudinal direction. The oscillating guide rollers are governed by respective actuators as a function of the data supplied by sensors that detect the position of the edges of the web.

The system of correction with oscillating guide rollers could raise problems in the case where openable and recloseable absorbent sanitary products are to be produced. In this case, the longitudinal edges are provided at regular intervals with closing elements of the microhook type that are coupled to one another after folding of the composite web. The absorbent sanitary products of a recloseable type are frequently provided with side panels, usually elasticized, which bear one of the two microhook closing elements, as described in the documents Nos. EP-A-1523968 and EP-A-2025311.

The system of correction of the alignment of the edges described in the document No. EP-A-1504738 could damage the microhook closing elements or else could cause problems of alignment of the edges on account of the presence along the edges of discontinuities formed by the folded side panels.

OBJECT AND SUMMARY OF THE INVENTION

The object of the present invention is to improve the technique for folding a composite web in such a way that the opposite longitudinal edges of the composite web can be easily controlled to maintain the condition of mutual alignment.

According to the present invention, said object is achieved by an apparatus and a method forming the subject of claims 1 and 7.

The claims form an integral part of the teaching provided herein in relation to the invention.

BRIEF DESCRIPTION OF THE DRAWINGS

The present invention will now be described in detail with reference to the attached drawings, which are provided purely by way of non-limiting example and in which:

FIG. 4 is a schematic perspective view of an absorbent product obtained with an apparatus and a method according to the present invention;

FIG. 5 is a schematic top plan view of the product of FIG. 4;

FIG. 6 is a schematic perspective view illustrating a variant of the product of FIG. 4.

DETAILED DESCRIPTION OF EMBODIMENTS

Figure 1:
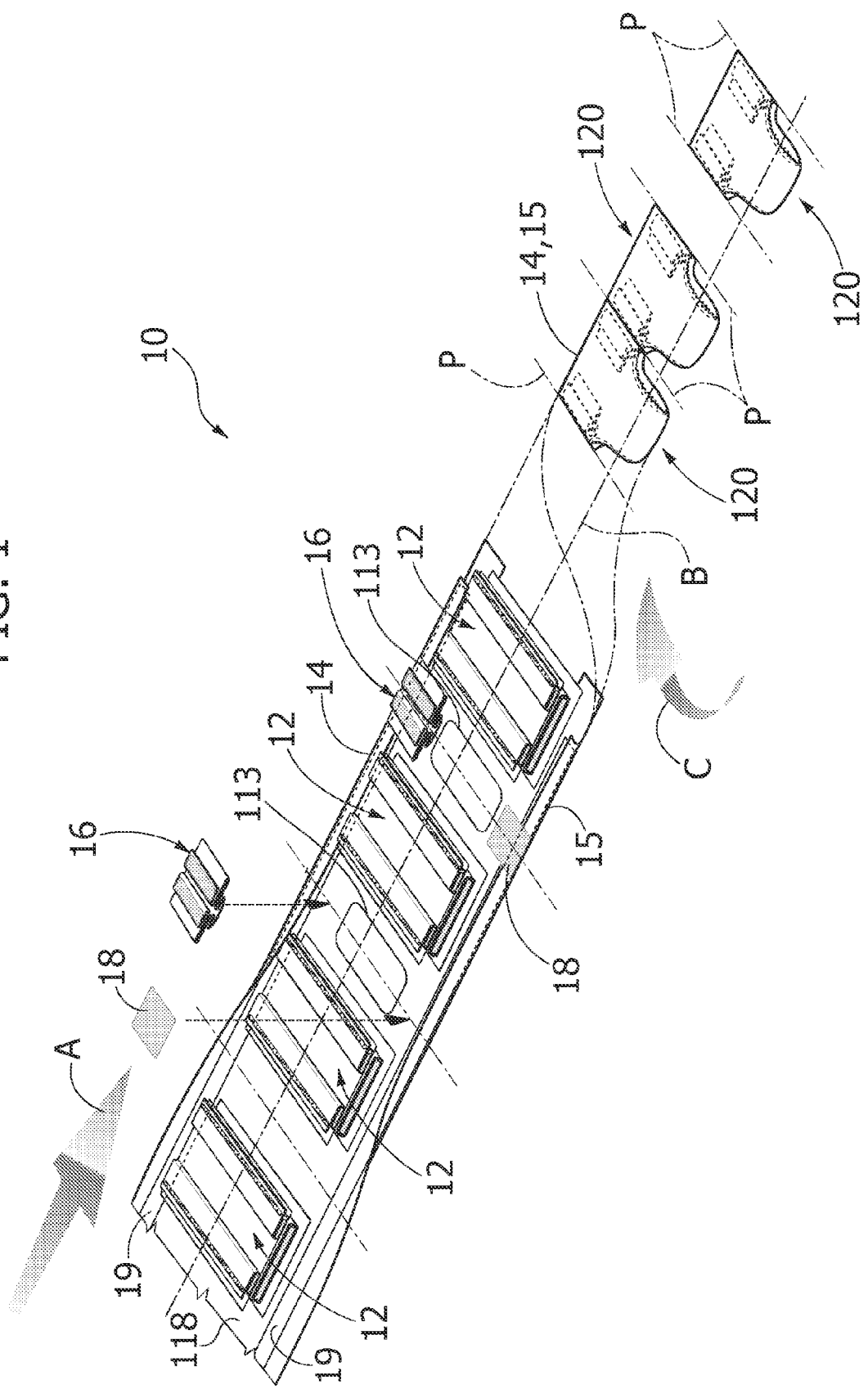
FIG. 1 is a schematic perspective view illustrating the step of folding of a composite web in a process for the production of absorbent sanitary products that can be worn like pants.

Illustrated in the ensuing description are various specific details aimed at an in-depth understanding of the embodiments. The embodiments may be provided without one or more of the specific details, or with other methods, components, materials, etc. In other cases, known structures, materials or operations are not illustrated or described in detail so that various aspects of the embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in one embodiment" or "in one embodiment" that may be present in various points of the present description do not necessarily refer to one and the same embodiment. Moreover, particular conformations, structures, or characteristics can be combined adequately in one or more embodiments.

The references used herein are merely provided for convenience and hence do not define the sphere of protection or the scope of the embodiments.

With reference to FIG. 4, the reference number 100 designates a disposable absorbent product of the so-called "pull-on" or "training pant" type obtained with a method and an apparatus in accordance with the teachings provided by the present invention.

Basically, the product 100 is made up of an absorbent central body or insert 12, which is to come into contact with the body of the user, is able to assume a general U shape, and is suited to absorbing and withholding the body fluids. The absorbent insert 12 is moreover positioned on a chassis 114 that comes into contact with the garments of the user, and is characterized in that it is able to maintain the absorbent insert 12 in the correct working position, even when it is weighed down by the liquids absorbed.

The absorbent insert 12 has a structure in which there may be recognized (in addition to various other accessory elements):

- a top layer or topsheet 13 permeable to the evacuated body liquids, which is to face the body of the user;
- a bottom layer or backsheet 115 impermeable to the body liquids, which is to face the outside, i.e., the chassis 114; and
- an absorbent core 116 set between the topsheet 13 and the backsheet 115, which is designed to absorb and withhold the body fluids.

Present on the absorbent insert 12 are other characteristic elements that contribute to increasing the characteristics of wearability and absorbency of the insert 12 itself, such as for example the elastics for the legs 117 that contribute to getting the absorbent product 100 to adhere to the body of the end user and the so-called cuffs or elasticized sides 119 set at the sides of the absorbent core 116 with the function of lateral containment of body fluids.

For a more detailed description of the characteristic elements listed above and of others, well known to persons skilled in the sector, the reader is referred to the extensive literature existing on the subject, such as, for example, U.S. Pat. No. 4,704,116 granted on Nov. 3, 1987 to Enloe.

The chassis 114 is made up of at least one sheet of non-woven fabric 118, or other adequate material, on which elastic materials in threads and/or in strips 19, such as, for example, Lycra threads produced by Invista and/or the strips of synthetic rubber produced by Fulflex, are made to adhere.

The aforesaid elastic materials are rendered fixed with respect to the sheet of non-woven fabric 118 of the chassis 114 by means of adhesives or by means of sealing obtained with heated rollers or ultrasound systems. Normally set on top of the elastic materials is a further sheet of non-woven fabric 17, which can come from another sheet of fabric or may be made of the same material 118 appropriately chosen wider than necessary and subsequently folded inwards to cover the elastic elements 19.

Made on the chassis 114 is a shaped cut 113 that delineates the boundary of the openings for the legs.

As is evident to a person skilled in the art, the representations of FIGS. 4 and 5 are of a schematic nature and are intended to highlight the fact that the method and the apparatus forming the subject of the present invention can be applied to a wide variety of possible types of embodiment of the product 100.

Particular types of preclosed absorbent product for which the present invention is particularly advantageous are amply described in the document Nos. EP 1 523 968 A1 and EP 2 057 975 B1. In particular, designated by 120 in FIG. 6 is an absorbent product provided according to the teachings of the document No. EP-A-2057975.

Represented schematically in FIG. 1 is the process of production of an absorbent sanitary product 120. Designated by 10 in FIG. 1 is a composite web, formed by a chain of semifinished products of absorbent sanitary products 120, which advances continuously in a longitudinal direction A. The composite web 10 has two opposite longitudinal ends 14 and 15, which on the product form, respectively, the front waist border and the rear waist border. Said edges, during the process of production of the absorbent sanitary product, are set on top of one another following upon a fold along a line of longitudinal folding B parallel to the longitudinal direction A. The arrow C indicates schematically the movement of folding that leads to obtaining superposition of the longitudinal edges 14 and 15. After folding about the longitudinal axis B, the longitudinal edges 14 and 15 set on top of one another are connected together at regular intervals. As represented in the embodiment of FIG. 4, said connection can be obtained by means of the two seals 110 or else, in the embodiment illustrated in FIG. 6, by means of openable and recloseable closing elements 16 and 18, as described in greater detail in the document No. EP-A-2057975, filed in the name of the present applicant. After the operations of folding and closing, the continuous composite web is subjected to operations of cutting along transverse lines P to form single products 120. In the embodiments illustrated in FIGS. 4 and 6, the respective products 100 and 120 are training-pants that can be of the type closed in a permanent way on the sides, as illustrated in FIG. 4, or else with openable and recloseable side panels, as represented in FIG. 6.

The composition, structure, and process of formation of the continuous composite web 10 are not described in detail in so far as they fall outside the scope of the present invention. It will be appreciated from FIG. 1 that in a production process where the semifinished products 120 extend transversely with respect to the direction of movement it is necessary to ensure that during the operation of folding about the longitudinal axis B the opposite longitudinal edges 14 and 15 are properly aligned with one another. The present invention regards specifically the way in which alignment of the longitudinal edges 14 and 15 is made following upon the operation of folding about the axis B.

Figure 2:
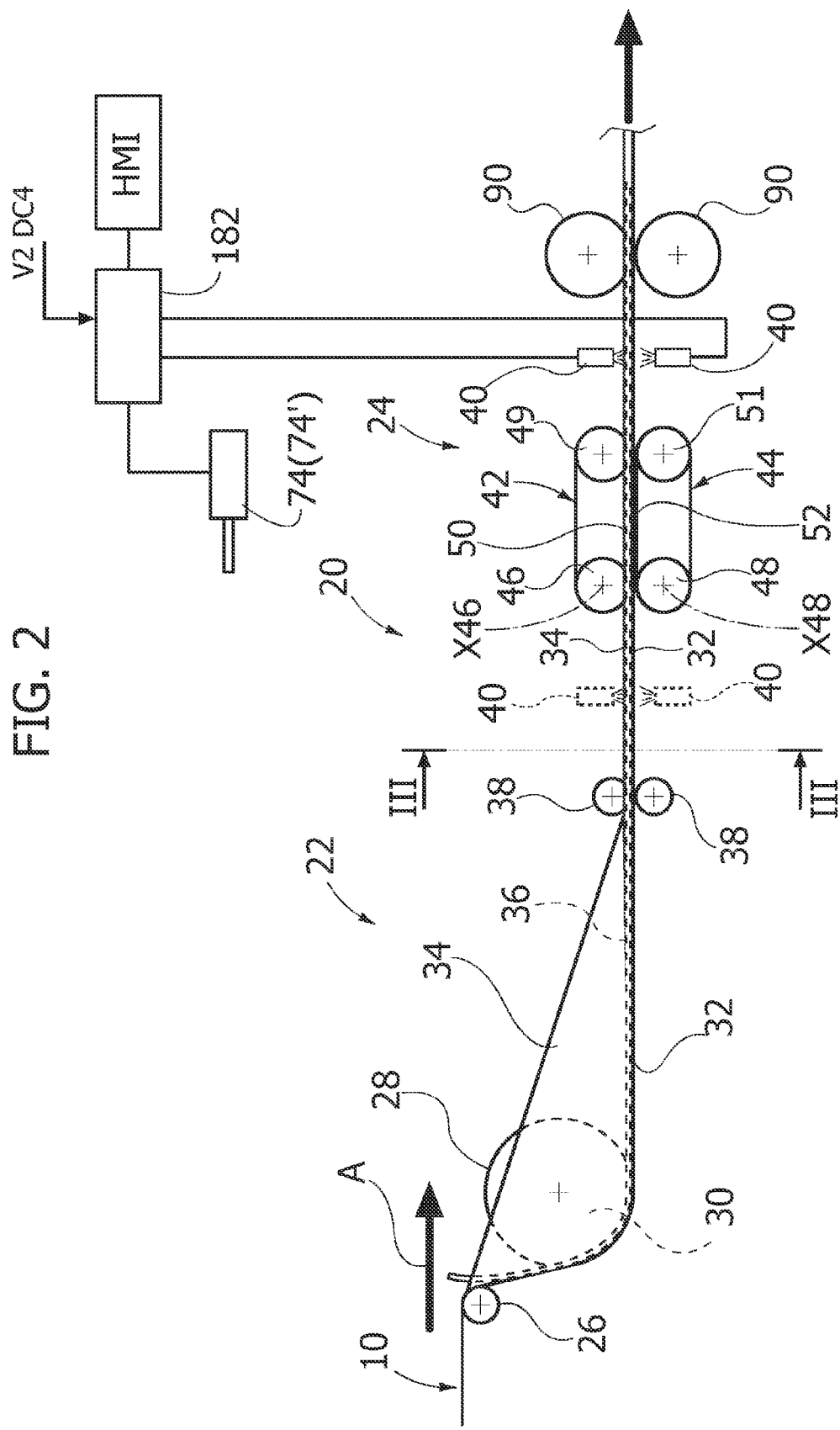
FIG. 2 is a schematic side view of an apparatus for folding a composite web.

FIG. 2 is a schematic illustration of an apparatus 20 according to the present invention that effects the longitudinal folding of the composite web 10 and mutual alignment of the opposite longitudinal edges. The apparatus 20 comprises a folding station 22 and an alignment station 24, set downstream of the folding station 22.

In one embodiment, the folding station 22 comprises a transverse transmission roller 26 and a folding wheel 28, which is able to turn about an axis transverse to the longitudinal direction A. The folding wheel 28 has a front face 30 contained in a plane orthogonal to the composite web formed by the chain of semifinished products of absorbent sanitary products 120, and hence positioned along the centre line of the composite web 10, i.e., of the line of fold B, in so far as the aforesaid lines coincide. The folding wheel 28 effects a preliminary fold of the continuous web 10 in two sections 32, 34 set on opposite sides with respect to the line of longitudinal folding B. In the embodiment schematically illustrated in FIG. 2, a first section of web 32 is run over the circumference of the folding wheel 28 and a second section 34 passes into contact with the front face 30 of the folding wheel 28. The folding section 22 moreover comprises a longitudinal-folding bar 36 that extends along the line of fold B, i.e., along the centre of the web formed by the semifinished products 120. The two sections of web 32, 34 are folded on one another around the folding bar 36. The folding section 22 terminates with a pair of transverse guide rollers 38, between which the two sections of web 32, 34 folded on one another are passed.

It is evident to a person skilled in the sector that the folding section 22 is not able to ensure that the opposite longitudinal edges 14 and 15 of the continuous web 10 are aligned with one another at the end of the fold. For this reason, downstream of the folding section 22 the alignment section 24 is provided, which effects a correction of the relative position of the edges 14 and 15 in the case where said edges are not aligned with one another and do not present the required precision of alignment.

The alignment section 24 comprises one or more sensors 40 designed to detect the position of each of the longitudinal edges 14 and 15 or the relative position of one of the two ends with respect to one another. In the example illustrated in FIG. 2, two sensors 40 are provided, each of which detects the position of a respective longitudinal edge 14 or 15.

Detection devices adequate for this type of control are linear-array sensors model DAC 005, produced by Fife-Titland GmbH, Fifestrasse 1, (D) 65779 Kelkheim, Germany.

A measurement of the error of alignment between the longitudinal edges 14 and 15 is obtained by comparing with one another the measurements of position of the two sensors 40, by means of a processor or control and command system 182.

An appropriate control system for this type of work is digital processor model D-MAX-2 designed and manufactured by Fife-Titland GmbH, Fifestrasse 1, (D) 65779 Kelkheim, Germany.

Figure 3:
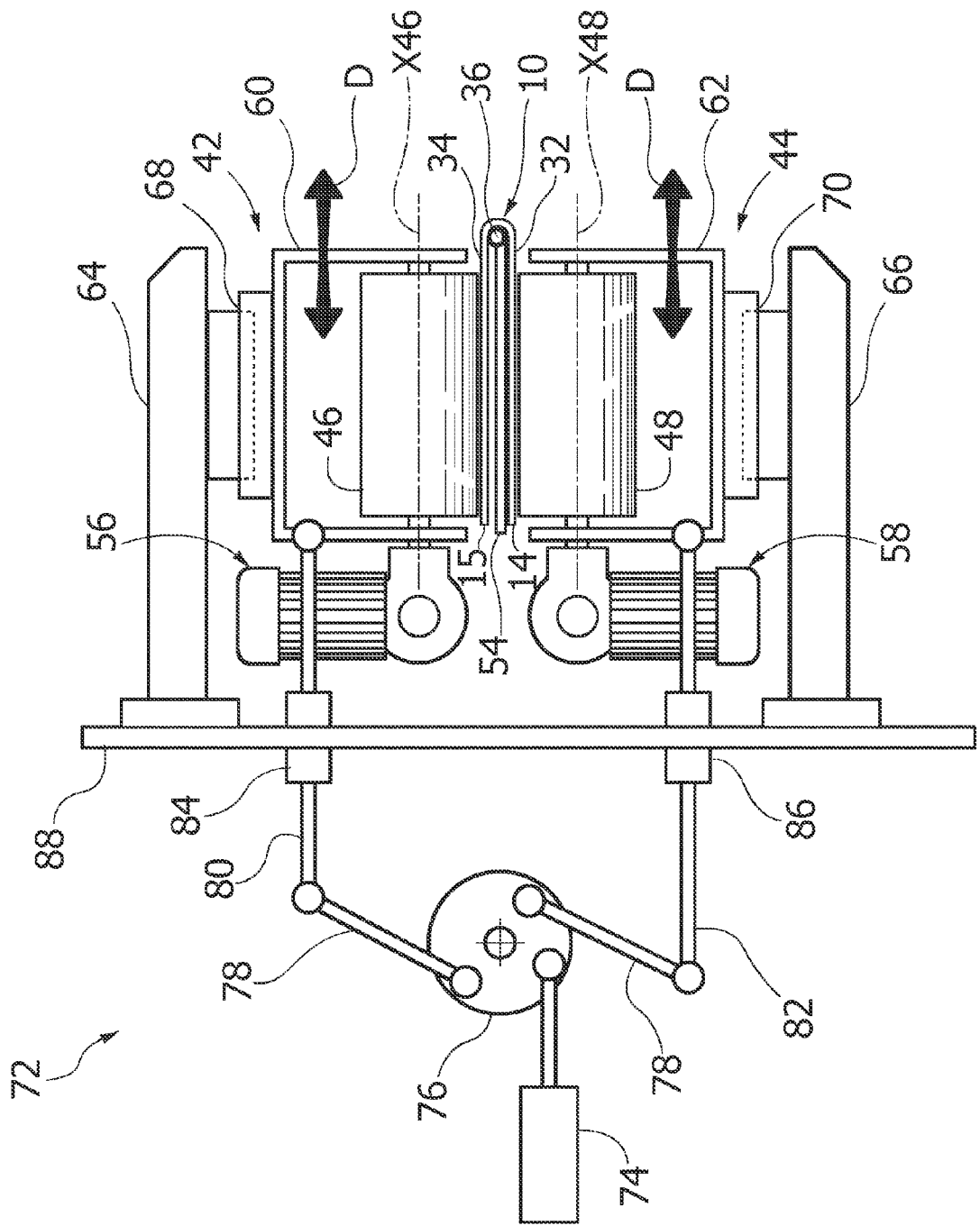
FIG. 3 is a schematic cross-sectional view according to the line III-III of FIG. 2.

With reference to FIGS. 2 and 3, the alignment section 24 comprises two suction belt conveyors 42 and 44 set on opposite sides of the folded sheet 10. The suction belt conveyors 42 and 44 have respective input transmission rollers 46 and 48 that can turn about respective transverse axes X46 and X48, perpendicular with respect to the longitudinal direction A. The suction belt conveyors 42 and 44 have respective branches 50 and 52 facing one another, and respective motor-driven output transmission rollers 49 and 51.

In a preferred embodiment, as may be appreciated better from the view of FIG. 3, the alignment section comprises a stationary separation plate 54, which extends between the branches 50 and 52 of the conveyors 42 and 44 and has the purpose of separating the two sections 32, 34 of the web 10 from one another. The aforesaid embodiment is particularly advantageous and appreciated in the case where the sanitary product that is being processed by the apparatus forming the subject of the present invention is provided with elements for closing the edges of a re-openable type. The branches 50, 52 of the belt conveyors 42, 44 are connected to a source of sub-atmospheric pressure and are designed to obtain gripping by suction of the respective sections of web 34, 32 located on opposite sides of the separation plate 54.

The belt conveyors 42, 44 are motor-driven, and the respective branches 50, 52 move in the direction A at the same rate at which the web 10 advances in a longitudinal direction. With reference to FIG. 3, the conveyors 42, 44 comprise respective motor-reducer assemblies 56, 58, which drive respective rollers 49, 51 in rotation.

The belt conveyors 42 and 44 comprise respective mobile frames 60 and 62, which bear the shafts for rotation of the transmission rollers 46 and 48, as well as the axes of the motor-driven rollers 49 and 51 and the respective motor-reducer assemblies 56, 58. The frames 60 and 62 are both mobile in a direction D transverse with respect to the longitudinal direction A. In one embodiment, as may be appreciated better in the view of FIG. 3, the frames 60 and 62 are connected to respective stationary bases 64, 66 by means of respective linear guides 68 and 70, which enable the movement of the supporting assemblies 60, 62 in the transverse direction D.

The belt conveyors 42, 44 are associated to a control device 72 that moves the two conveyors 42, 44 jointly in opposite directions in the transverse direction D. The control device 72 is configured for moving the two mobile frames 60 and 62 of the conveyors 42, 44 simultaneously by an equal amount and in opposite directions. Alternatively, the control device 72 can be equipped with two actuators that enable the two mobile frames 60 and 62 of the conveyors 42 to move in a transverse direction D, 44 independently of one another.

In a preferred embodiment, the control device 72 comprises an actuator 74 designed to govern rotation of an element 76, which is able to turn about a longitudinal axis. The element 76 is connected by means of connecting rods 78 to two rods 80, 82 fixed to respective mobile frames 60, 62. The rods 80 and 82 are guided in a transverse direction D by respective guides 84, 86 carried by a stationary wall 88. The rods 80, 82 are set on opposite sides with respect to the axis of rotation of the rotary element 76. The arrangement of the connecting rods 78 means that a movement of rotation of the rotary element 76 produces movements of the same amplitude and in opposite directions of the rods 80, 82. Consequently, by means of the actuator 74 it is possible to govern movements of the same amplitude and in opposite directions of the belt conveyors 42, 44 in the transverse direction D. A linear motor suitable for this type of use is the linear digital actuator model D-LAB-3A-5-050.1-ISCT produced by Fife-Titland GmbH, Fifestrasse 1, (D) 65779 Kelkheim, Germany.

Figure 7:
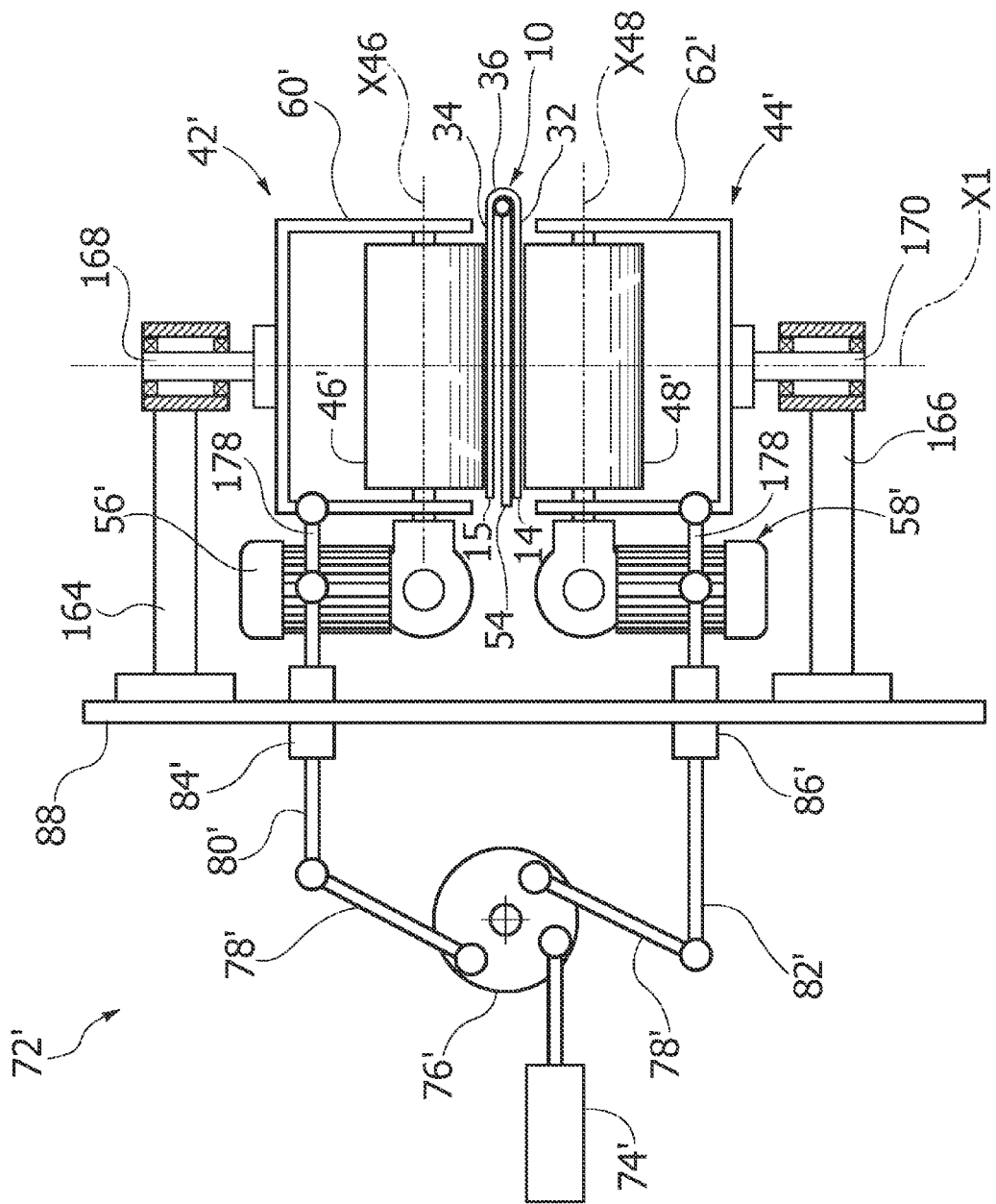
FIG. 7 is a schematic cross-sectional view illustrating a second embodiment of the apparatus according to the invention.

In one embodiment, as may be appreciated better from the view of FIG. 7, the belt conveyors 42' and 44' comprise respective mobile frames 60', 62', which bear the shafts for rotation of the transmission rollers 46', 48' and the respective motor-reducer assemblies 56', 58'. The frames 60' and 62' both rotate about the axis X1, which is perpendicular both to the line of fold B and to the axes of the transmission rollers 46' and 48' of the respective belt conveyors 42' and 44'. The axis X1 is moreover set at the centre of the rollers 46' and 48' in such a way as to intersect the axes of rotation X46 and X48. In this way, the transverse displacement in the direction D of the belt conveyors 42' and 44' is zero in the point where the sheets come into contact with the input rollers 46' and 48' of the respective belt conveyor and is maximum where the sheets abandon the aforesaid respective conveyor 42' and 44', i.e., at the output rollers 49 and 51.

In one embodiment, the aforesaid frames 60' and 62' are connected to respective stationary bases 164 and 166 by means of the pins 168 and 170, where each of said pins turns within a pair of bearings of appropriate dimensions and loading characteristics.

The belt conveyors 42' and 44' are associated to a control device 72', which moves the two conveyors 42' jointly in opposite directions in the transverse direction D, 44'. The control device 72' is configured for moving the two mobile frames 60' and 62' of the conveyors 42' and 44' simultaneously to an equal extent and in opposite directions.

In one embodiment, as may be appreciated better from the view of FIG. 7, the control device 72' comprises an actuator 74' designed to govern rotation of an element 76', which is able to turn about a longitudinal axis. The element 76' is connected by means of connecting rods 78' to two rods 80', 82', which are in turn connected, thanks to the connecting rods 178, to the respective rotating frames 70' and 62'. The rods 80', 82' are guided in a transverse direction D by respective guides 84', 86' carried by a stationary wall 88. The rods 80', 82' are set on opposite sides with respect to the axis of rotation of the rotary element 76'. The arrangement of the connecting rods 78' and 178 means that a movement of rotation of the rotary element 76' produces movements of the same amplitude and in opposite directions of the rods 80', 82' and consequently rotations of the same amplitude, but in the opposite direction, of the belts conveyors 42', 44'. Consequently, by means of the actuator 74' it is possible to govern rotations of the belt conveyors 42' and 44' of the same amplitude and in opposite directions in the transverse direction D. Also in the embodiment of FIG. 7, the control device 72' can be equipped with two actuators that enable the two mobile frames 60' and 62' of the conveyors 42', 44' to move in a transverse direction D independently of one another.

In the embodiment represented in FIG. 2, the actuator 74 is governed as a function of the signals received by the sensors 40 that detect the position of the longitudinal edges 14 and 15 of the two sections of web 32, 34. The sensors 40 can be set upstream or downstream with respect to the conveyors 42 and 44, as indicated with a solid line and with a dashed line, respectively, in FIG. 2.

Set downstream of the alignment section 24 are two closing rollers 90, which have the purpose of connecting together the opposite edges 14 and 15 at intervals of constant pitch after the alignment of the edges of the web has been made. In the case where the composite web 10 is equipped with openable and recloseable closing elements 16, 18 the closing rollers 90 are simply pressure rollers that press together the closing elements downstream of the separation plate 54 that keeps said elements separate. In the case where the composite web 10 is without openable and recloseable closing elements, the closing rollers 90 can be sealing rollers designed to perform intermittent sealing of the aligned edges 14 and 15.

The movement in a transverse direction in opposite directions of the belt conveyors 42, 44 enables alignment of the edges 14 and 15 of the two sections of folded web 32, 34, without stretching the web 10 in a transverse direction. The system of alignment of the edges according to the present invention enables a precise alignment of the edges even in the case where there is a significant error of misalignment after the folding operation. The suction belt conveyors 42, 44 effect gripping of the respective sections of web 34, 32 on the outer faces and do not damage the openable and recloseable closing elements that may be present on the internal faces of the web. The separating plate 54 keeps the openable and recloseable closing elements separate until the alignment of the edges has been completed and prevents the closing elements from attaching to other parts of the web.

Of course, without prejudice to the principle of the invention, the details of construction and the embodiments may vary widely with respect to what is described and illustrated herein, without thereby departing from the scope of the invention, as defined by the ensuing claims.

The invention claimed is:

1. An apparatus for folding in two a continuous web that advances in a longitudinal direction (A), comprising:
   a folding station designed to fold said continuous web along a line of longitudinal folding (B) parallel to said longitudinal direction (A); and
   an alignment station for mutual alignment of opposite longitudinal edges of said continuous web,
   wherein the folding station is upstream of an inlet of the alignment station, so that at the inlet of the alignment station the continuous web is folded in two and has two portions overlapping each other,
   wherein the alignment station comprises two suction belt conveyors having respective branches facing and parallel to each, designed to pick up by suction respective overlapping portions of the continuous web, and
   wherein said suction belt conveyors are mobile in a transverse direction (D) and are associated to a control device designed to move said suction belt conveyors by the same amount and in opposite directions in said transverse direction (D) as a function of information on the position of said longitudinal edges.

2. The apparatus according to claim 1, wherein the apparatus comprises a separation plate set between said facing branches of said suction belt conveyors.

3. The apparatus according to claim 1, wherein said suction belt conveyors comprise respective frames mobile in a transverse direction (D) on respective rotation pins.

4. The apparatus according to claim 1, wherein said control device comprises a rotary element, which is able to turn about a longitudinal axis and is connected to two rods mobile in said transverse direction (D) in mutually opposite directions, each of said rods being connected to a respective frame of the respective suction conveyor belt.

5. The apparatus according to claim 4, wherein said rotary element is driven in rotation about said longitudinal axis by means of an actuator governed by sensors designed to detect the position of respective longitudinal edges of respective folded sections of said continuous web.

6. A method for folding in two a continuous web that advances in a longitudinal direction (A), comprising the following steps and using the apparatus according to claim 1:
   folding said continuous web along a line of longitudinal folding (B) parallel to said longitudinal direction (A); and
   aligning to one another opposite longitudinal edges of said continuous web,
   wherein said step of mutual alignment of opposite longitudinal edges of said continuous web comprises the steps of:
   picking up opposite folded sections of said continuous web by means of respective suction belt conveyors having respective branches facing one another; and
   correcting the relative position of said longitudinal edges by means of a relative displacement of said suction belt conveyors by the same amount and in mutually opposite directions in a transverse direction (D).

7. The method according to claim 6, wherein during said step of correction of the relative position of said edges the opposite folded sections of said continuous web are set on opposite sides of a separation plate.

* * * * *